United States Patent [19]

Rucinski

[11] Patent Number: 5,830,197
[45] Date of Patent: Nov. 3, 1998

[54] WOUND IRRIGATION DEVICE AND METHOD

[75] Inventor: Paul J. Rucinski, Gainesville, Fla.

[73] Assignee: Innovation Technologies, Inc., Gainesville, Fla.

[21] Appl. No.: 824,999

[22] Filed: Mar. 26, 1997

Related U.S. Application Data

[63] Continuation of Ser. No. 464,039, Jun. 5, 1995, abandoned, which is a continuation of Ser. No. 259,416, Jun. 14, 1994, abandoned.

[51] Int. Cl.$^6$ ............................................. A61M 35/00
[52] U.S. Cl. ........................... 604/290; 604/310; 128/898
[58] Field of Search ..................................... 604/289, 310, 604/311, 290, 277, 278, 36, 37, 73, 79; 128/898; 137/801; 239/327, 542, 552, 558, 559; 222/565, 212, 215

[56] References Cited

U.S. PATENT DOCUMENTS

| | | |
|---|---|---|
| 1,863,158 | 6/1932 | Greene . |
| 1,920,245 | 8/1933 | Cronford ................................. 604/278 |
| 1,986,061 | 1/1935 | Hill . |
| 2,219,141 | 10/1940 | Ritz . |
| 2,757,667 | 8/1956 | Bronk .................................. 128/200.14 |
| 2,883,983 | 4/1959 | Biederman . |
| 2,990,563 | 7/1961 | Davidson . |
| 3,583,602 | 6/1971 | Gruber et al. . |
| 4,093,124 | 6/1978 | Morane et al. ..................... 128/200.14 |
| 4,108,178 | 8/1978 | Betush ............................... 128/200.14 |
| 4,112,947 | 9/1978 | Nehring ..................................... 604/28 |
| 4,300,555 | 11/1981 | Kopito ..................................... 604/310 |
| 4,336,861 | 6/1982 | Sentell et al. ........................... 604/278 |
| 4,357,937 | 11/1982 | Burrell, Jr. et al. . |
| 4,421,505 | 12/1983 | Schwartz .................................. 604/28 |
| 4,668,227 | 5/1987 | Key ........................................ 604/277 |
| 4,692,159 | 9/1987 | Kuzemchak ............................ 604/277 |
| 4,740,206 | 4/1988 | Allander ................................. 604/310 |
| 4,767,416 | 8/1988 | Wolf et al. ......................... 128/200.14 |
| 4,804,373 | 2/1989 | Bloxom ................................... 604/277 |
| 4,810,250 | 3/1989 | Ellenberg et al. ...................... 604/277 |
| 4,892,526 | 1/1990 | Reese ..................................... 604/310 |
| 4,923,448 | 5/1990 | Ennis ................................. 128/400.14 |
| 4,968,298 | 11/1990 | Michelson . |
| 5,059,187 | 10/1991 | Sperry et al. ........................... 604/310 |
| 5,071,104 | 12/1991 | Witt et al. . |
| 5,133,701 | 7/1992 | Han . |
| 5,201,726 | 4/1993 | Kirkham ................................. 604/310 |

FOREIGN PATENT DOCUMENTS

| | | |
|---|---|---|
| 147284 | 8/1931 | Germany . |
| 1377120 | 2/1988 | U.S.S.R. ................................. 604/28 |
| 425867 | 3/1935 | United Kingdom ................... 604/310 |

OTHER PUBLICATIONS

Dire, D.J. et al. (1990) "A Comparison of Wound Irrigation Solutions Used in the Emergecy Department" Annals of Emergency Medicine 19(6):143–147.

Sinkinson, C.A. ed. (1989) "Maximizing a Wound's Potential for Healing" Emergency Medicine Reports 10(11):83–89.

Lammers, R.L. (1991) "Soft Tissue Procedures: Principles of Wound Management" Clinical Procedures in Emergecy Medicine, pp. 515–522.

Cracroft, D. (1987) "Minor Lacerations and Abrasions" Emergency Medicine: A Comprehensive Review, pp. 107–109.

Mulliken, J.B. (1984) "Management of Wounds" Emergency Medicine, pp. 283–286.

*Primary Examiner*—Mark O. Polutta
*Attorney, Agent, or Firm*—Saliwanchik, Lloyd & Saliwanchik

[57] ABSTRACT

A method for irrigation of a wound, said method comprising a reservoir housing containing a wound irrigation solution and a discharge means attachable thereto, said discharge means having at least one port therethrough wherein said port, or ports forms a nozzle for directing a pressurized dispersed stream of said solution.

2 Claims, 4 Drawing Sheets

WOUND IRRIGATION DEVICE AND METHOD

This is a continuation of application Ser. No. 08/464,039, filed Jun. 5, 1995 now abandoned, which is a continuation of application Ser. No. 08/259,416, filed Jun. 14, 1994 now abandoned.

BACKGROUND OF THE INVENTION

In the management and treatment of a wound (defined herein to mean any injury or opening in tissue) there are three primary objectives: (1) prevention of infection, (2) preservation and/or restoration of function, and (3) preservation and/or restoration of cosmetic appearance. The most important of these objectives is the prevention of infection. Success in the prevention of infection directly affects the healing process and the degree to which the other two objectives, function and cosmetic appearance, can be preserved and/or restored.

In the case of wounds, the presence of bacteria is the single cause of infection. It is known that the number of bacteria, rather than bacterial type, is a critical determinant of whether a wound becomes infected. Experimental evidence suggests that a critical level of bacteria is approximately $10^5$ organisms per gram of tissue. Below this level, wounds heal; at levels greater than $10^5$ bacteria per gram of tissue, wounds often become infected. All traumatic wounds are contaminated by the time the wound is presented to a medical care facility for treatment (Dire, Daniel I. [1990] "A comparison of Wound Irrigation Solutions Used in the Emergency Department," *Annals of Emergency Medicine* 19(6):704–708). Dirty wounds, or those which have not been treated within six hours, are likely to be contaminated with bacteria at levels which are higher than the critical level. Reducing the number of bacteria in and around the wound is a recognized and accepted means for avoiding infection and expediting wound healing.

Different procedures of wound management have been developed to help decrease the level of bacteria present in a wound, i.e., reduce the incidence of infection. The cleansing of a wound and the site surrounding the wound to remove blood clots, debris, dirt, or other foreign materials which can introduce contaminants, including pathogenic microorganisms, is critical in reducing levels of bacteria in and around the wound. There are numerous wound cleansing procedures presently used by healthcare professionals such as debridement, excision and irrigation. See, for example, Sinkinson, Craig Alan, ed. (1989) "Maximizing A Wound's Potential For Healing," *Emergency Medicine Reports* 10(11):83–89; Lammers, Richard L. (1991) "Soft Tissue Procedures: Principles of Wound Management," in *Clinical Procedures in Emergency Medicine*, Roberts and Hedges, eds., 2nd Ed., W.B. Saunders Company, pp. 515–521; Cracroft, Davis (1987) "Minor Lacerations and Abrasions," *Emergency Medicine*: A Comprehensive Review, Kravis and Warner, eds., 2nd cd., Aspen Publishing Co., pp. 107–110; and Mulliken, John B. (1984) "Management of Wounds," in *Emergency Medicine*, May ed., John Wiley & Sons, pp. 283–286.

Irrigation is the most commonly used procedure for cleansing of open contaminated wounds.

Irrigation involves the application of sterile solutions or fluids to wounds to remove loose devitalized tissue, bacterial inoculum, blood clots, loose debris, and foreign bodies proximate to and within the depths of the wound. The two critical components of any effective wound irrigation method and/or device are: (1) the application of an adequate volume of sterile irrigation solution to the wound, and (2) the use of sufficient pressure applied in an effective dispersal pattern in the delivery of the solution to effectively remove contaminants. Regarding volume, the amount of irrigation solution required will depend upon the type of wound and the level of contamination. Injuries which can introduce a high amount of bacteria into a wound (such as puncture wounds and bites) may require 1 liter or more of irrigation solution. See Mulliken, 1989. Regarding pressure, it has been demonstrated that stream pressure of a minimum of 7 pounds per square inch (psi) is required to effectively flush or remove contaminants from a wound. Irrigation pressure in excess of desired limits (e.g., 25 psi or greater) may actually drive bacteria and particulate matter deeper into the wound and thereby defeat the purpose of the irrigation process. High-pressure irrigation may also cause damage to healthy tissue and impede the tissue's defenses and retard healing. Thus, effective wound irrigation requires the use and application of adequate volumes of irrigation solution delivered to the wound in an effective dispersal pattern at appropriate pressures.

Bulb syringes or gravity flow irrigation devices deliver fluid at low pressures and as such are ineffective in ridding wounds of small particulate matter or in sufficiently reducing wound bacterial counts. Irrigation by bulb syringe exerts a pressure of about 0.05 psi, which does not reduce the number of bacteria or particulate contaminants enough to prevent infection. The flow rate of irrigation fluid delivered through intravenous (IV) tubing can be enhanced by inflation of a blood pressure cuff around a collapsible plastic IV bag. This method is cumbersome and provides considerably less irrigation pressure than can be delivered by a plunger-type syringe.

The plunger-type syringe is the most common irrigation device currently used. Its use involves filling the barrel of the syringe with sterile irrigation solution and depressing the plunger to generate and apply a single pressurized stream of solution in and around the wound to dislodge and rinse away contaminants. This device has two notable disadvantages: (1) an extremely limited reservoir of irrigation fluid (typically a syringe with a 35 cc-capacity barrel), and (2) it is limited to dispersal and application of a single concentrated stream of solution to the wound. Consequently, in most cases, the syringe must be repeatedly refilled in order to apply sufficient quantities of irrigation solution to a wound. This is time-consuming and cumbersome to do while attempting to maintain a sterile field. In an attempt to address this limitation, a device has been developed that involves a system consisting of a syringe and IV tubing with a valve system that attaches to a bottle of saline to provide a ready means of refilling the syringe barrel. (Travenol pressure irrigation set, code no. 2D2113, or irriget, Ackrad Laboratories, Garwood, NJ). Additionally, U.S. Pat. No. 4,357,937 describes a disposable, manually operable medical irrigation device which is adapted for providing selective volume and stream intensity in liquid flow from a plurality of syringes. These devices do not adequately address the disadvantages of using syringes for irrigation as discussed above and are not commonly used in clinical practice due to their complexity of use and cost.

The amount of hydraulic pressure that can be delivered with a plunger-type syringe varies with the force exerted on the plunger of the syringe and with the internal diameter of the attached needle. Plunger-type syringe devices that deliver moderate pressure employ either a 19 gauge needle attached to a 35 cc syringe, which creates hydraulic pressure in the range of 7–8 psi, or a 30 ml syringe fitted with a 19 gauge needle which typically creates about 7 psi irrigation pressure. A 22 gauge needle attached to a 12 cc syringe, delivers a pressure of about 13 psi. Such pressures have been proven effective in wound irrigation, but, as stated above, such devices apply only a single stream of solution to the wound. In addition, these described devices hold less than adequate volumes of irrigation solution and therefore require repeated refilling which is time consuming and cumbersome.

U.S. Pat. No. 5,071,104 describes a wound irrigation apparatus and process for cleansing wounds which includes a pressure bladder, e.g., a blood pressure cuff, disposed proximate a reservoir holding a cleaning solution. The device in the '104 patent also includes a flexible tubular conduit for transmitting the solution from the reservoir to a single nozzle. The conduit and reservoir form a two-part system which is time consuming to set up, inconvenient to use, and costly.

U.S. Pat. No. 5,133,701 describes a disposable pressurized wound irrigation device which has a pressurized chamber for providing a force upon the reservoir such that a single liquid stream of cleansing solution is expelled from the device at a constant pressure. A propellant is used in evacuating the cleanser contents of the device. This invention requires a propellant and involves a relatively elaborate manufacturing and filling process which is labor intensive and requires specialized machinery. This device is also inconvenient to use and costly.

The subject invention successfully addresses the above described disadvantages associated with the previously known devices and methods, and provides certain attributes and advantages which have not been realized by these known devices.

BRIEF SUMMARY OF THE INVENTION

The subject invention concerns a novel and inexpensive method and device for convenient and effective manual wound irrigation. In one embodiment the subject invention provides a discharge means for a standard reservoir housing containing an adequate volume of irrigation solution wherein the discharge means has a plurality of nozzles through which the irrigation solution can pass. In a preferred embodiment the reservoir housing, upon which the discharge means is affixed, is compressible or squeezable (e.g., plastic bottles in which the saline solutions are presently available). The medical or health care professional or other person using the subject device and providing wound irrigation therapy can compress the reservoir housing to force the irrigation solution through the nozzles under sufficient pressure to dislodge dirt, debris, or other particles, including microorganisms, e.g., pathogenic bacteria.

In another embodiment, elongated ports are used to achieve the desired dispersal of the stream of irrigation solution.

The object of the subject invention is to provide an easy to use, economical wound irrigation method and device which are capable of delivering adequate volumes of irrigation solution (without refilling the reservoir) in a dispersed stream under sufficient pressure to effectively cleanse the wound thereby reducing the incidence of infection.

The subject invention would allow the medical professional to, without assistance, easily direct and control the application of irrigation solution with one hand, leaving the other hand free for other activities such as separation of the wound to further facilitate irrigation.

DETAILED DESCRIPTION OF THE INVENTION

The subject invention, is a novel convenient, inexpensive and effective device which comprises, in a preferred embodiment, a reservoir housing and a discharge means for irrigation of a wound. The subject invention also includes a method of use for the device. The materials and methods of the subject invention make it possible, for the first time, to conveniently and easily apply a stream of wound irrigation fluid to a wound with the stream having an appropriate volume, pressure, and dispersal pattern. Unlike previous attempts to provide wound irrigation devices, the current invention is particularly advantageous in its simplicity and its ability to provide a physician with excellent control over the irrigation process. Under optimal circumstances, the devices and methods of the subject invention will be utilized by trained emergency technicians; however, because of the simplicity and convenience of the subject invention, it can be used to greatly enhance the effectiveness of wound irrigation regardless of the training level of the person performing the irrigation.

Figure 1:
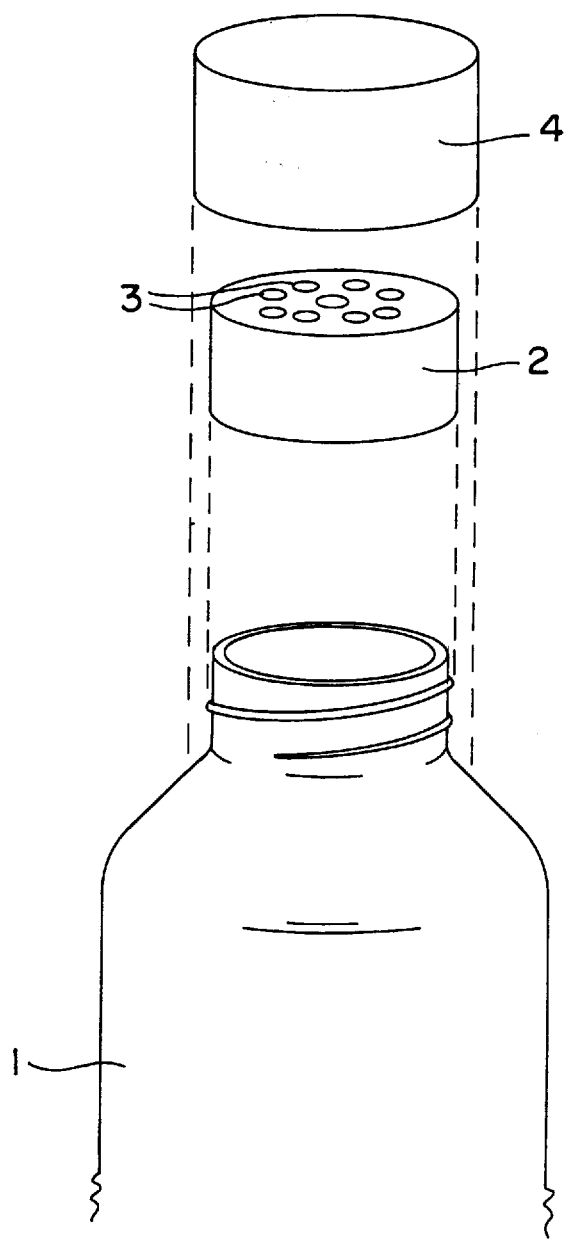
FIG. 1 shows the subject wound irrigation device which includes a compressible reservoir housing, and a discharge means which has a plurality of ports which form nozzles for directing pressurized streams or a shower of irrigation solution to the wound.

The subject invention is perhaps best understood by reference to the accompanying figures. FIG. 1 shows an embodiment of the subject invention wherein the device comprises a squeezable reservoir housing having a wall 1 which forms a reservoir which can contain therein a wound-cleaning material. The reservoir can preferably hold a liquid solution (e.g., sterile saline) as the wound cleansing solution for irrigating, and thereby removing particles or other contaminants from, a wound. The reservoir housing has a mouth or opening which communicates the reservoir to the outside of the housing. Disposed over the reservoir housing opening, and affixed to the reservoir housing is a discharge means 2. In one embodiment, the discharge means has a plurality of ports 3, each port forming a circular nozzle whereby the irrigation solution in the reservoir passes through in a pressurized and directional manner. As described herein, other embodiments of the subject invention utilize slits or combinations of slits and circular ports to achieve the advantageous fluid dispersion which is critical to the subject invention. As used herein, the term nozzle refers to either circular ports or elongated ports such as slits. As described herein, a critical feature of the subject invention is the unique use of these nozzles to easily and conveniently achieve a stream of irrigation solution having the appropriate volume, pressure and dispersal pattern to obtain effective wound irrigation which can greatly enhance the safe and speedy recovery from wounds.

As used herein, reference to a "dispersed" stream of solution means that the area from which the stream emanates, or the area which it contacts, is larger than that which can be achieved using a syringe. In one embodiment, the dispersed stream can be achieved using multiple ports. The ports can be presented in a variety of patterns such as a circular pattern. Alternatively, the dispersed stream can be achieved using an elongated port, such as a slit. The use of slits can also take advantage of a variety of patterns including slits which from arcs or slits which cross to form an "X" shape or asterisk shape. Combination of slits and circular ports can also be used.

A removable protective shield 4, which is disposable or reattachable can be included, if desired, to cap and protect the discharge means and the contents of the reservoir housing.

The discharge means is a particularly advantageous embodiment of the invention. The discharge means can be affixed to the reservoir housing. The discharge means can be, for example,size as the opening of t approximately the same size as the opening of the reservoir housing. In one embodiment, the discharge means can have a plurality of ports therethrough, each port forming a separate nozzle which allows the contents of the reservoir to pass directly through during use of the invention. Each of the ports can be of any desirable size, preferably less than one-eighth inch in diameter and having a size between about a 10 gauge hypodermic needle and about a 30 gauge needle, and most preferably having a size ranging from that of a 16 gauge needle to a 25 gauge needle. Each of the nozzle-forming ports can be the same size or the ports can be different sizes and shapes. The different sizes of ports allow for the liquid to be expelled from the discharge means at different pressures. For example, the 16 gauge port allows for a stream having about 6 psi pressure when the device is squeezed by the normal adult; the 25 gauge port provides a pressure of up to about 20 psi from each nozzle.

Figure 2:
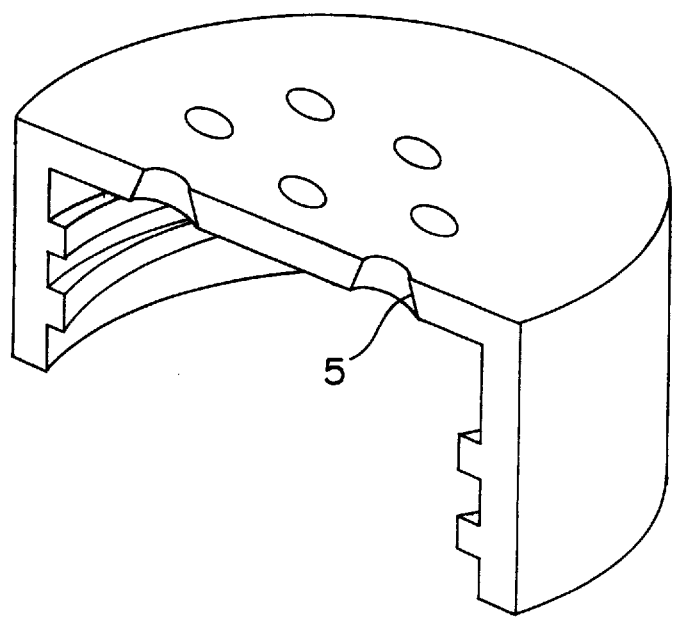
FIG. 2 shows a sectional view of the discharge means illustrating the cone shaped design of the ports forming the nozzles which direct a pressurized stream of irrigation solution.
Figure 3:
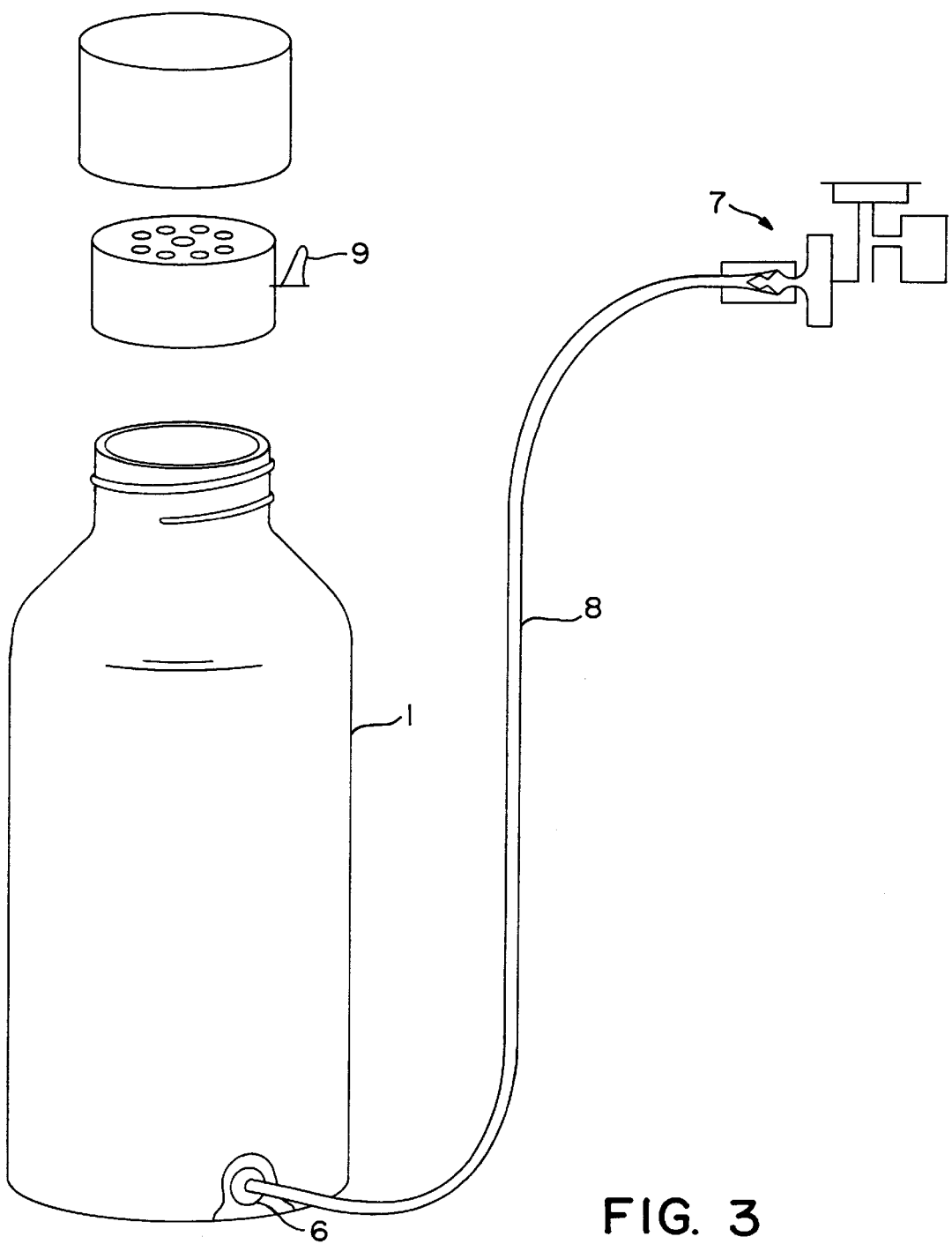
FIG. 3 shows an embodiment of the subject reservoir housing having incorporated therein an inlet port 6 for supplying pressurized gas from a source 7 to the reservoir 1. The inlet port can be part of a fitting for affixing thereto a delivery tube 8, which thereby delivers the pressurized gas to the reservoir from the pressurized gas source.
Figure 4:
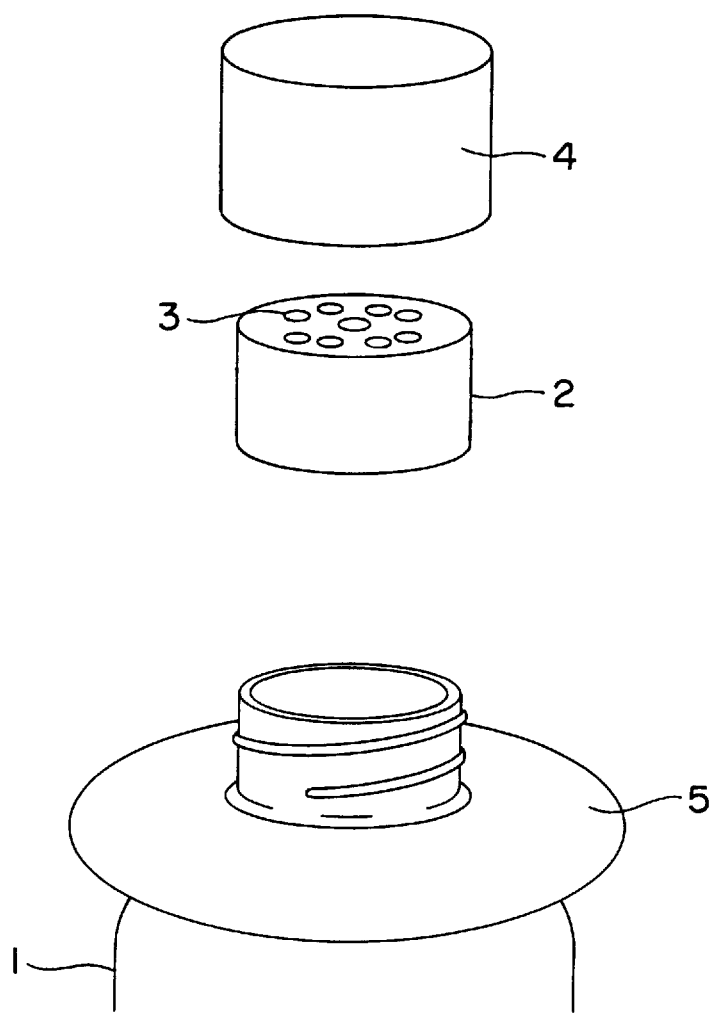
FIG. 4 shows the embodiment of the device comprising a discharge means and reservoir housing, which includes a back-splash protective shield component.

In a preferred embodiment, each port is cone-shaped, forming a nozzle traversing the discharge means. The nozzle has a larger diameter on the inner face of the discharge means and a smaller diameter on the outside face of the discharge means. This embodiment of cone-shaped ports is shown as 5 in FIG. 2. In one embodiment, the wall of the cone-shaped nozzle is formed at an angle of about 60 degrees from the perpendicular. Advantageously, the cone shape of each nozzle allows for hydrostatic pressure to keep the nozzle filled with liquid thus lubricating the surface of the device in the unlikely event that the wound is inadvertently contacted with the discharge means during the irrigation process. Alternatively, the ports can be cylindrical instead of cone shaped.

The nozzles can also be formed in different configurations in order to optimize the irrigation action for particularly desired results. For example, one nozzle design comprises a 19 gauge (needle size) central nozzle surrounded by a circularly disposed row wherein the circle formed by the row of nozzles has a diameter of about 1 cm. The circularly disposed row consists of about eight (8) nozzles in one embodiment of the invention, which are spaced evenly apart from one another. At least two, and preferably four, of these nozzles, alternatingly configured, are formed in such a way that the stream of liquid expelled from the discharge means is directed at an angle of 45–85 degrees from the surface of the discharge means. The angle of these ports is preferably between 75 degrees and 85 degrees and is most preferably about 82 degrees from the surface of the discharge means. The remainder of the nozzles, including the center nozzle, direct a stream at about a 90-degree angle from the top surface. The preferred configuration allows the stream from each of the nozzles angled at 82 degrees to intersect with the stream from the center nozzle at about 25 cm from the outer surface of the discharge means.

In another embodiment, the discharge means can include decreased nozzle size which can generate a greater stream pressure (22 gauge needle size). This embodiment preferably includes at least one additional circularly disposed row either outside or inside the circularly disposed row as described for the embodiment above. The circularly disposed rows form nozzles which are disposed in a configuration of concentric rings. An additional circularly disposed row of nozzles can increase the volume of irrigation solution used in the irrigation process. Alternatively, increasing the diameter of the nozzles can allow greater volume of irrigation solution to be directed at the wound. Preferably, the additional circularly disposed row is an outer row which comprises eight (8) additional nozzles approximately 1 cm outward, radially, from the center nozzle. The number of nozzles can vary from as little as 2 to as many as 24 or more as desired. Most preferably at least two, and typically four, of the nozzles in the outer row, in an alternating basis, would direct a stream of the solution contained therein at an angle of about 75 to 85 degrees when discharged by pressure created by squeezing of the bottle. As would be appreciated by one skilled in the art having the benefit of this disclosure, elongated ports (slits) can be used to achieve essentially the same dispersal pattern as that which is produced using the holes as discussed herein.

One embodiment of the subject invention also includes a removable or partially detachable protective shield, which is placed over the discharge means to protect the ports and contents of the reservoir from contamination or premature discharge or leakage. The protective shield can comprise a screw-cap which threadably engages the neck of a discharge means, a snap-on cap which is detachably affixed to the discharge means or neck of the reservoir housing using a latch, hook, or other locking or connecting means, or a hinged cover commonly referred to as a "flip-top" cap. The hinged cover can be permanently affixed to the discharge means or can be part of a threadably engaged screw-cap or protective shield.

A second type of protective shield can also be provided as a component of the subject device. This second type of protective shield is a "back-splash" protective shield wherein the back-splash protective shield is detachably or permanently affixed to the device, preferably between the discharge means and the compressible reservoir housing. The back-splash protective shield protects the health care professional from back-splash of human and or animal body fluids which are mixed with and splashed from the wound when the wound is contacted by the discharged irrigation solution.

The wall of the reservoir housing can be made or molded from any material which is preferably rigid enough to stand upright when the reservoir is filled with irrigation solution. In a typical embodiment, the reservoir housing is formed by a molded plastic which is pliable enough so that the wall of the reservoir housing can be squeezed or compressed by hand to exert pressure on the contents of the reservoir. Other materials can also be used for the reservoir housing walls, including rubber, laminated or plastic-lined paper, a composite material, or the like, as would be readily understood in the art. These materials are commercially available. The preferred embodiment comprises a plastic material which is pliable enough to squeeze by hand and which also has resilience properties to return to its original shape when no longer compressed or squeezed.

The horizontal cross-sectional shape of the reservoir housing can be square, rectangular, cylindrical, or other geometric shapes as desired or as already available. The walls can be tapering toward one end or the other. Alternatively, other shapes can be made for the reservoir housing according to and adapted for a particular use. For example, part of the reservoir housing wall can be slightly rounded as in a general hourglass shape or can be molded according to ergonomic consideration for easily fitting a hand or otherwise facilitating handling or compressing the reservoir housing. The reservoir formed by the housing of the subject invention can typically hold a volume of about 100 ml to 1000 ml, preferably about 250 ml to about 750 ml and most preferably about 500 ml.

Further, in a preferred embodiment, the reservoir housing comprises at one end a mouth and a neck portion formed at the mouth end. The neck portion of the reservoir housing is generally at least slightly smaller in diameter than the diameter or diagonal measurement of the reservoir housing. The neck of the reservoir housing forms a connecting means, e.g., threads, for affixing the discharge means thereto. The reservoir housing neck is preferably integrally molded with the reservoir housing, but can be formed or molded separately and affixed to the mouth end of the reservoir housing. The material used for the neck portion of the reservoir housing can be the same as the material used to make the reservoir housing cylinder.

Alternatively, the neck portion can be a different material, for example, a more rigid or sturdy material than the compressible material forming the reservoir housing wall. For example, the material used to make the neck portion can be a metal or a hard plastic, or the like.

The neck portion can be formed having threads, or latches, or other connecting means for affixing the discharge means thereto. The connecting means can be on the outer face of the neck portion, forming a male connecting end, or can be on the inner face forming a female connecting end of the neck portion.

The discharge means can have connecting means complementary and attachable to the neck portion. In a preferred embodiment, the neck portion and discharge means can have threads or grooves so that the discharge means can be detachably and/or threadably engaged to the neck portion of the reservoir housing. This screw-top design can be made to be adaptable to available irrigation solution bottles. Thus, the discharge means of the subject invention is interchangeable, when desired, with the screw-cap which is provided with an irrigation solution bottle as are available. The screw-top design provides the user with the option of using the reservoir housing with the nozzle-forming ports or to threadably remove the discharge means and pour out or change the irrigation solution.

Another embodiment of the discharge means includes a stopper which can be forced or wedged into the mouth of a reservoir housing. The stopper can have a flange which facilitates positioning of the stopper by preventing its insertion completely through the opening of the reservoir housing and into the reservoir. In another embodiment, the discharge means can be affixed directly to the reservoir housing or neck portion of the reservoir housing so that the discharge means fits flush with the mouth of the reservoir housing.

This flush-fitting embodiment of the discharge means is formed as an integral part of the reservoir housing wherein the discharge means is molded with, or heat-sealed to, the reservoir housing. An alternative embodiment is a flush-fitting discharge means which is held in place over the mouth of the reservoir housing with a connecting ring threadably engaging the threaded neck of the reservoir housing. The discharge means is held in place by having a rib or groove which corresponds to and engages a groove or flange on the threaded connecting ring.

Another embodiment of the subject invention includes a reservoir housing comprising an inlet port and fitting for attaching a flexible tubing for delivery of pressurized gas to the reservoir. A pressurized irrigation reservoir would employ an embodiment of a squeezable reservoir housing that can be attached to an outside pressure source. Pressure sources generally available in hospitals, emergency rooms, and other medical clinics or facilities provide a pressure of 0–55 pounds per square inch (PSI). The reservoir would attach via a flexible tube to the pressure source connector and to the fitting provided on the reservoir housing of the subject device. Supplying to the reservoir an outside source of pressurized gas would permit the medical professional to discharge the irrigation solution obtained in the reservoir at a constant pressure. A valve can also be incorporated into the inlet port fitting, the reservoir housing, and/or the discharge means to stop the flow of air pressurizing the reservoir or to stop the flow of irrigation solution discharged from the discharged means. This permits interruption of the wound irrigation process, and thus control, by the user as desired. Alternatively, the reservoir could itself be pressurized so that no external pressure source is necessary. In this embodiment, the reservoir could be manufactured to contain a pressurized gas to expel the irrigation fluid with the desired force. The pressurized gas could be separated from the fluid by, for example, a diaphragm.

The irrigation solution used can be water, saline, or a balanced salt solution. The solution is preferably sterile and at the discretion of the user or manufacturer of the irrigation solution can additionally comprise an antibacterial and/or antifungal component. The device can be sterilized by known sterilization techniques, including boiling, autoclaving, gas sterilization and the like, either separately or together with the reservoir housing.

Buffered Ringer's solution or commercially available balanced salt solution (e.g., Tis-U-Sol or Physio-Sol) are physiologically compatible and are commonly used in wound irrigation procedures.

The antiseptic agents most commonly used in wound care at present include:

Povidone-iodine solution (Betadine preparation)-iodine added to the carrier polyvinylpyrrolidone (PVP), a water-soluble organic complex; this combination is called an iodophor. Standard solutions of Betadine preparation are 10 per cent.

Povidone-iodine surgical scrub (Betadine scrub)-the iodophor PVP-I and an anionic detergent (pH 4.5).

pHisoHex-an emulsion of an anionic detergent, entsulfon, lanolin cholesterols, petrolatum, and hexachlorophene (pH 5.5).

Hi-Bi-clens-chlorhexidine gluconate plus a sudsing base (pH 5.1 to 6.5).

Tincture of green soap-potassium oleate, isopropanol, potassium coconut oil, soap.

Dakin's solution 0.2 per cent solution hypochlorite solution.

Hydrogen peroxide-an oxidizing agent.

Benzalkonium chloride (Zephiran)-a quaternary ammonium compound that works as a cationic surface active agent.

Nonionic surfactants-Pluronic F-68 (Shur-Clens) and Poloxamer-188 (Pharma Clens)-agents that have no antimicrobial activity (pH 7.1).

From the description of the device hereinabove, a method of using the subject device would readily be understood and adaptable by those persons having ordinary skill in the art. The reservoir housing is filled with a desired irrigation solution. The irrigation solution is sterilized before or after filling. The reservoir housing and contents can be stored in a sterile environment, e.g., sterile packaging which is opened immediately prior to use. In a preferred use, the protective shield is removed, then the reservoir housing can be directed towards the wound and squeezed or compressed to expel or discharge the solution in the desired direction, and at the desired pressure to effect irrigation of a wound to remove contaminants or debris. See also the Example, provided below.

It would also be understood that the described discharge means can be packaged separately from the reservoir housing. The discharge means is packaged in a sterile environment. In a preferred use of the embodiment wherein the discharge means is provided separately from the reservoir housing, the cap of a readily available, squeezable irrigation bottle containing a sterile irrigation solution, e.g., normal saline, is replaced with the subject discharge means. The bottle, now having the subject discharge means attached or engaged thereto, can be used as described herein.

Significantly, it is known that more force is required to rid the wound of particles with a small surface area (e.g., bacteria) than to remove particles with a large surface area (e.g., dirt, sand, or vegetation). Minimum recommended volumes of irrigation solution vary, but for a moderately sized potentially contaminated wound, for example a laceration 3–6 cm long and less than 2 cm deep, 200 to 300 ml should be used. Greater volumes, on the order of one to two liters, may be required for larger or heavily contaminated wounds. Irrigation should continue at least until all visible, loose particulate matter has been removed.

Following is an example which illustrates procedures, including the best mode, for practicing the invention. This example should not be construed as limiting. All percentages are by weight and all solvent mixture proportions are by volume unless otherwise noted.

EXAMPLE 1
METHODS OF WOUND IRRIGATION

When a patient presents a wound to a medical or other health care professional skilled in the art, that medical professional assesses the extent of the injury sustained by the patient, including all other life threatening injuries. Appropriate action regarding these life threatening injuries is performed and a history is recorded. All wounds are covered to minimize further contamination until the actual repair process begins.

For examination of the wound, it is assumed that a medical professional would have performed a detailed evaluation of the extent of tissue injury, including but not limited to: anatomical area considerations, depth of the wound, type of injury, e.g., crush injury, puncture wound, bites, missiles, cuts with sharp objects, or the like. Included in this examination would be a determination of the type(s) of contamination, time elapsed between the occurrence of the injury to presentation, gross contamination of a wound, and other medical factors associated with an increase incidence of infection (for example, diabetics, AIDS patients, and chemotherapeutics patients).

The wound and surrounding tissue, at the option of the health care professional, could be anesthetized using topical, local, or general anesthetics before the wound-cleansing method begins.

In one embodiment, the subject device has a discharge means affixed to a reservoir housing as described with a protective shield covering the discharge means. The health care professional using the subject device would remove the protective shield to expose the discharge means. The subject device can be held in either hand as preferred by the user. Normally, it would be held in the dominate hand in a bottle-holding fashion. This allows the medical care professional to gently open the wound if needed, with the opposite hand, preferably protected by a sterile glove, to expose the depths of the wound.

Once the depths of the wound have been exposed, the end of the reservoir housing having the discharge means affixed thereto is directed towards the wound. Manual or mechanically produced pressure is applied to the reservoir housing to expel the irrigation solution through the nozzles of the discharge means. The wound should be irrigated in this fashion until all visible evidence of contamination has been removed. A potentially contaminated wound of any size should be irrigated with a minimum of 200–300 ml of irrigation solution. Heavily contaminated or larger wounds may require 2–3 liters of irrigation solution. The health care professional could vary the angle of the discharged irrigation solution from the discharge means in reference to the wound to further assist with the dislodgement of contaminants. This variation in the angle will also decrease or increase the amount of back-splash. Thus it would be important to irrigate in a manner that decreases the back-splash. Minimizing back-splash is achieved by irrigation at acute angles to the plane of the wound.

Following an initial irrigation of the wound, a re-examination of the wound should be undertaken. The wound should be explored to its base to ascertain that no visible foreign bodies or contaminants remain. If foreign bodies or contaminants are found, the irrigation process should be repeated followed by a re-examination. This may continue for several cycles.

Once irrigation has been completed, i.e., no visible contaminants remain, the would be repaired in a standard accepted fashion.

It should be understood that the example and embodiment described herein is for illustrative purposes only and that various modifications or changes in light thereof will be suggested to persons skilled in the art and are to be included within the spirit and purview of this application and the scope of the appended claims.

I claim:

1. A method for irrigating a wound, said method comprising the steps of:
    (a) providing a sterile wound-irrigation solution in a compressible or pressurized reservoir housing having engaged thereto a discharge means comprising at least one port therethrough wherein said port forms a nozzle for directing a pressurized stream of said solution, and wherein the shape and configuration of said port, or ports, results in a dispersed stream of said solution;
    (b) directing the discharge means and reservoir housing so as to discharge the wound-irrigation solution toward said wound; and (c) discharging said wound-irrigation solution from said reservoir housing and through said nozzle-forming port or ports in said discharge means to produce a dispersed stream of said wound-irrigation solution directed at said wound, wherein said dispersed stream is applied with sufficient force to dislodge contaminants, thereby effectively irrigating said wound, and wherein the area from which said stream emanates, or the area which it contacts, is larger than that which can be achieved using a syringe.

2. A method for irrigating a wound, said method comprising the steps of:

(a) providing a wound-irrigation solution in a compressible or pressurized reservoir housing having engaged thereto a discharge means comprising at least two ports therethrough wherein said ports form nozzles for directing pressurized streams of said solution, and wherein the shape and configuration of said ports results in a dispersed stream of said solution;

(b) directing the discharge means and reservoir housing so as to discharge the wound-irrigation solution toward said wound; and (c) discharging said wound-irrigation solution from said reservoir housing and through said nozzle-forming ports in said discharge means to produce a dispersed stream of said wound-irrigation solution directed at said wound, wherein said dispersed stream is applied with sufficient force to dislodge contaminants, thereby effectively irrigating said wound, and wherein the area from which said stream emanates, or the area which it contacts, is larger than that which can be achieved using a syringe.

* * * * *

UNITED STATES PATENT AND TRADEMARK OFFICE
CERTIFICATE OF CORRECTION

PATENT NO. : 5,830,197
DATED : November 3, 1998
INVENTOR(S) : Paul J. Rucinski

It is certified that error appears in the above-identified patent and that said Letters Patent is hereby corrected as shown below:

Column 5, lines 22-23: "for example, size as the opening of t approximately the same size as the opening of the reservoir housing." should read --for example, a flat or domed disc of approximately the same size as the opening of the reservoir housing.--

Signed and Sealed this

Sixteenth Day of March, 1999

Attest:

Attesting Officer

Q. TODD DICKINSON

Acting Commissioner of Patents and Trademarks